United States Patent
Hymes

(10) Patent No.: US 6,455,065 B1
(45) Date of Patent: Sep. 24, 2002

(54) THERAPEUTIC METHOD FOR TREATING ACNE OR ISOLATED PIMPLES AND ADHESIVE PATCH THEREFOR

(75) Inventor: Alan C. Hymes, Mount Vernon, WA (US)

(73) Assignee: LecTec Corporation, Minnetonka, MN (US)

( * ) Notice: Subject to any disclaimer, the term of this patent is extended or adjusted under 35 U.S.C. 154(b) by 0 days.

(21) Appl. No.: 09/314,272

(22) Filed: May 18, 1999

(51) Int. Cl.[7] .............................. A61F 13/00; A61K 9/70
(52) U.S. Cl. ........................ 424/449; 424/400; 424/443; 424/447
(58) Field of Search ................................ 424/443, 444, 424/445, 446, 447, 449, 400, 402, 401

(56) References Cited

U.S. PATENT DOCUMENTS

| | | |
|---|---|---|
| 4,306,551 A | 12/1981 | Hymes et al. |
| 4,307,717 A | 12/1981 | Hymes et al. |
| 4,622,089 A | 11/1986 | Lauritzen |
| 4,671,266 A | 6/1987 | Lengyell |
| 4,675,009 A | 6/1987 | Hymes et al. |
| 4,920,158 A * | 4/1990 | Murray et al. .............. 523/111 |
| 5,476,443 A | 12/1995 | Cartmell et al. |
| 5,489,262 A | 2/1996 | Cartmell et al. |
| 5,501,661 A | 3/1996 | Cartmell et al. |
| 5,536,263 A | 7/1996 | Rolf et al. |
| 5,547,681 A | 8/1996 | Clark et al. |
| 5,643,589 A | 7/1997 | Chalmers |
| 6,096,333 A * | 8/2000 | Rolf et al. .................. 424/443 |
| 6,214,374 B1 * | 4/2001 | Schmirler et al. .......... 424/449 |

FOREIGN PATENT DOCUMENTS

| | | | |
|---|---|---|---|
| EP | 0 307 187 | 3/1989 | ............ A61L/15/03 |
| EP | 0 598 606 | 5/1994 | ............ A61L/25/00 |
| WO | 93/10163 | 5/1993 | |
| WO | 93/21899 | 11/1993 | ............ A61K/7/48 |
| WO | WO 97/48387 | 12/1997 | |
| WO | 99/17738 | 4/1999 | ............ A61K/9/06 |

* cited by examiner

*Primary Examiner*—Dameron L. Jones
(74) *Attorney, Agent, or Firm*—Schwegman, Lundberg, Woessner & Kluth, P.A.

(57) ABSTRACT

The skin disorder acne, as well as one or more isolated pimples, are treated by applying to the skin, over the skin disorder, a flexible moisture-containing hydrophilic hydrogel patch that includes a backing support such as paper, cloth or plastic and a water-based hydrogel layer applied to the backing. The hydrogel layer comprises a hydrophilic natural or synthetic polymer dispersed in water to provide body and can be a tacky adhesive. The polymer can comprise any high molecular weight hydrophilic carbohydrate such as karaya, cornstarch, or kelp and/or a synthetic hydrophilic polymer such as polyacrylamide or polyacrylic acid. A humectant such as an alcohol containing two or more hydroxyl groups, i.e., a polyhydric alcohol, keeps the adhesive layer moist. A solute such as salt, protein, sugar or an alcohol is dissolved in the water in a quantity sufficient to raise the osmotic pressure enough to maintain the adhesive hydrogel layer in a hypertonic state with respect to the underlying skin tissue. The hydrogel adhesive which hydrates the upper layer of skin forms a hydrophilic bridge with the patient's skin that allows fluid to be drawn by osmotic pressure from the skin disorder through the normally dry stratum corneum into the patch. Another aspect of the invention is the a hypertonic moisture-containing adhesive patch itself.

38 Claims, 3 Drawing Sheets

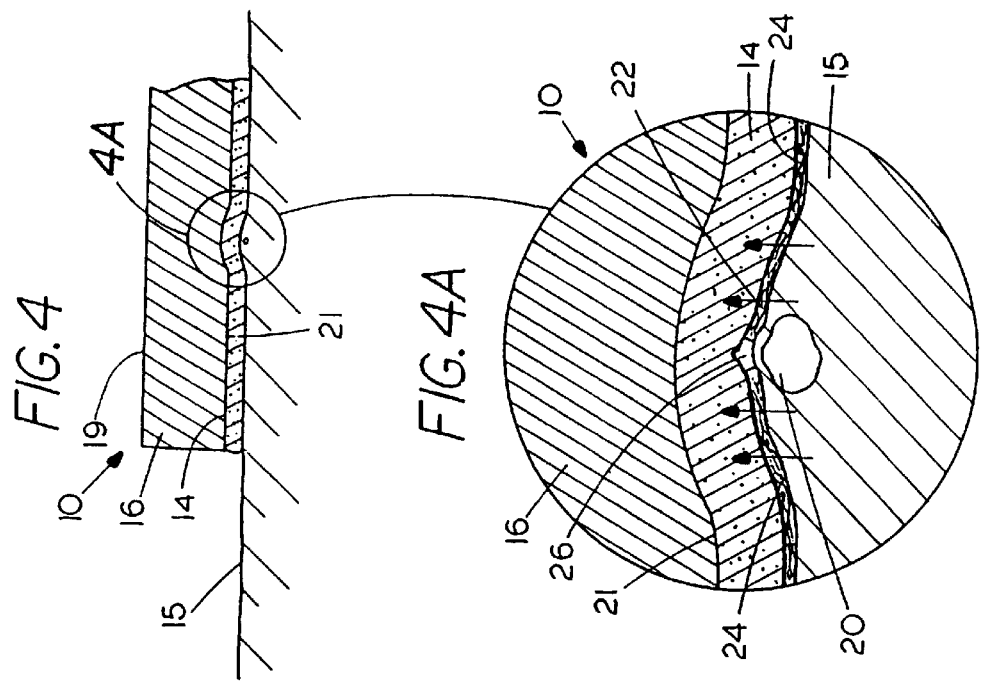
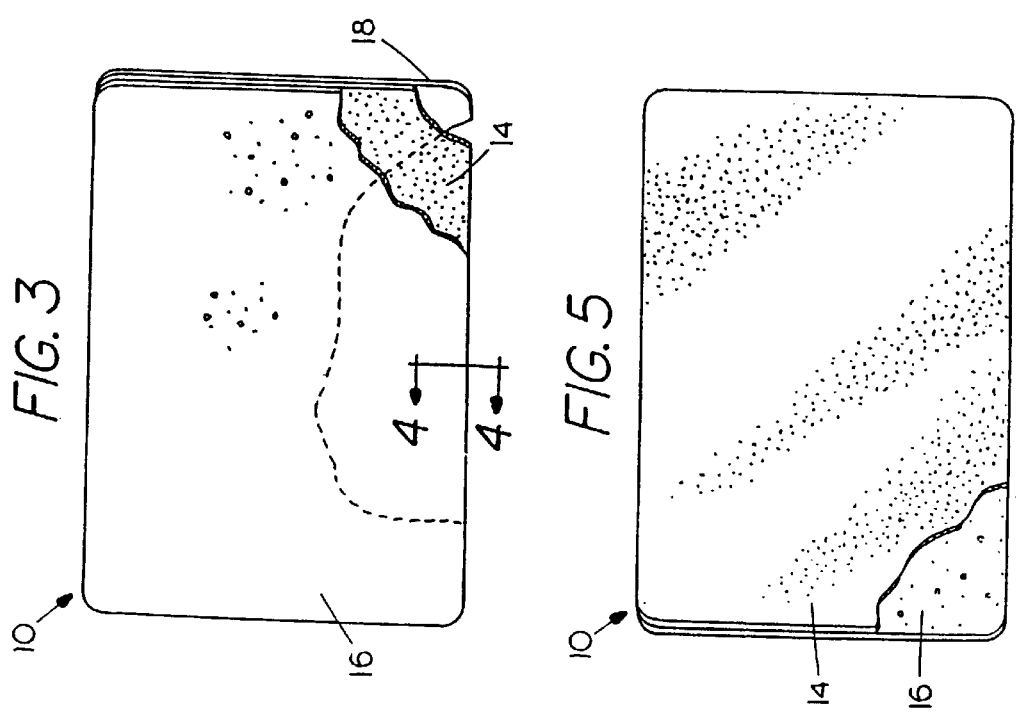

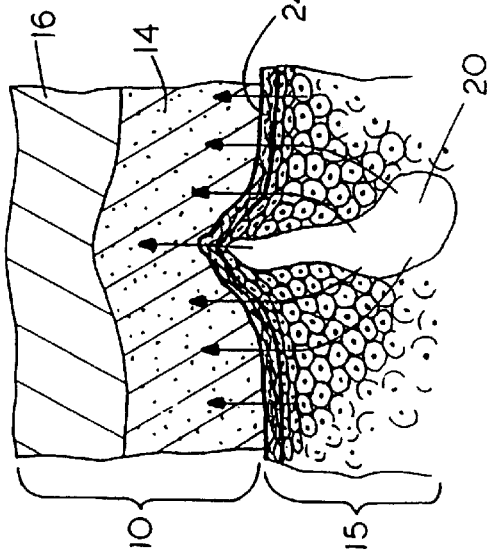
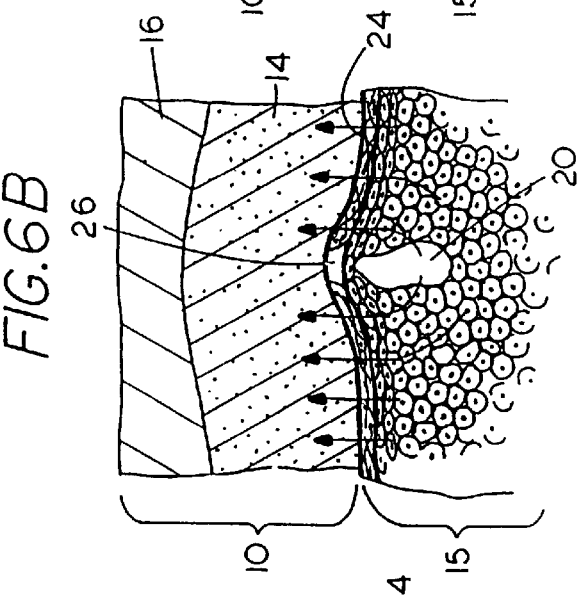
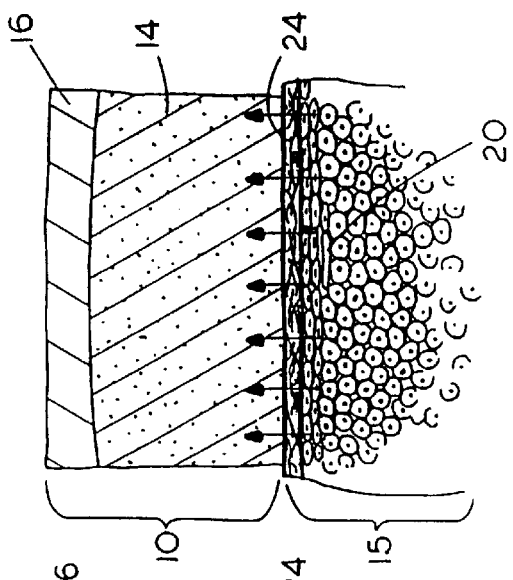

THERAPEUTIC METHOD FOR TREATING ACNE OR ISOLATED PIMPLES AND ADHESIVE PATCH THEREFOR

FIELD OF THE INVENTION

This invention relates to a method and therapeutic adhesive patch product for treating pimples and/or acne.

BACKGROUND OF THE INVENTION

Acne is a common inflammatory pilosebaceous disease characterized by comedones, papules, pustules, inflamed nodules, superficial pus-filled cysts, and (in extreme cases) canalizing and deep, inflamed, sometimes purulent sacs. Acne involves an interaction between hormones, keratinization, sebum, and bacteria that somehow determines the course and severity of acne. It often begins at puberty, when the increase in androgens causes an increase in the size and activity of the pilosebaceous glands. The earliest microscopic change is thought to be intrafollicular hyperkeratosis, which leads to blockage of the pilosebaceous follicle with consequent formation of the comedo, composed of sebum, keratin, and microorganisms, particularly *Propionibacterium acnes*. Lipases from *P. acnes* break down triglycerides in the sebum to form free fatty acids (FFA), which irritate the follicular wall. Retention of sebaceous secretions and dilation of the follicle may lead to cyst formation. Rupture of the follicle, with release of FFA, bacterial products and keratin constituents into the tissues, includes an inflammatory reaction that may result in abscess that heals with scars in severe cases. When the condition is less severe, it may merely involve an occasional isolated pimple. However, the underlying pathology is similar to that described above.

Current treatment begins by washing of the skin. However, even vigorous washing of the skin leaves behind billions of bacteria, yeasts and fungi that cannot be dispossessed no matter how vigorously one scrubs. Bacteria which is normally found deep in the hair follicles is harmless most of the time. However, during adolescence, when the sebaceous glands become particularly active, these bacteria can proliferate and cause an outbreak of acne. Current treatment often includes the use of specific follicular drugs such as benzoyl peroxide or retinoic acid; the removal of comedones; or the use of antibodies such as tetracycline, erythromycin, chlorohexidine gluconate, or oral isotretinoin. Present therapeutic methods are generally recognized as not entirely satisfactory. After treatment, many patients still continue to suffer from the symptoms of acne or pimples.

In view of these and other deficiencies of the prior art, it is an important object of the present invention to provide a treatment for acne or pimples that is safe and can be used by the patient for effectively relieving or improving one or more of the symptoms of acne or pimples.

Another object is to provide an adhesive patch for treating pimples and acne.

These and other more detailed and specific objects of the present invention will be better understood by reference to the following figures and detailed description which illustrate by way of example of but a few of the various forms of the invention within the scope of the appended claims.

SUMMARY OF THE INVENTION

The present invention provides a means of reducing extracellular fluid volume within the diseased skin in and around a pimple or acne outbreak where extracellular fluid accumulates and is associated with an infiltration of white blood cells. This reduction in volume is produced by contact with a hydrophilic hypertonic patch or gel over the diseased tissue to produce an osmotic imbalance between the liquid within the inflamed skin and the hydrogel layer within the patch. This osmotic imbalance draws fluid from the low concentration in the acne-infected skin to the high concentration in the hypertonic hydrogel. This invention therefore concerns a method for treating the skin disorder acne as well as one or more isolated pimples by applying directly to the diseased skin a flexible hypertonic hydrophilic moisture-containing patch. The patch includes a backing such as paper, cloth or plastic that acts as a support for the patch and a water-based hypertonic hydrogel layer applied to the backing that preferably has a tacky pressure-sensitive adhesive surface which bonds to the skin. The hydrogel layer bonds to the skin surface and forms a water bridge between it and the skin. The hydro bond allows the flow of fluid from the skin, which has a lower osmotic pressure than the osmotic pressure in the hydrogel layer.

The hydrogel layer comprises water and, as a thickening or gel forming agent, a hydrophilic natural or synthetic polymer dispersed in the water. The polymer can comprise a high molecular weight hydrophilic carbohydrate such as karaya, cornstarch, or kelp gel and/or a synthetic hydrophilic polymer such as polyacrylamide, a polyionic gel, or polyacrylic acid. A humectant such as an alcohol containing two or more hydroxyl groups, i.e., a polyhydric alcohol, is preferably employed to keep the adhesive layer moist. Any water soluble solute such as salt or an alcohol is dissolved in the water in a quantity sufficient to raise the osmotic pressure above that of the underlying tissue of the patient; namely, to a value over about 308 mOsmol/L so as to maintain the adhesive hydrogel layer in a hypertonic state with respect to the underlying tissue of the body. The hydrogel preferably, but not necessarily, has adhesive characteristics to bond the patch to the skin. Alternatively, the patch can be held against the skin by a sheet of adhesive tape, i.e., a bandage, connected thereto that is bonded to the skin on either side of the patch or by a non-adhesive wrap or binder. The hydrogel hydrates the outermost layer of skin. Consequently, the hydrogel adhesive, when applied to a patient, forms a hydrophilic bridge with the patient's skin which allows fluid transport between the skin and the patch across the hydrophilic bridge. With the patch in place on the skin, the fluid in and around the skin disorder is then transported from the skin to the hydrogel layer by osmotic pressure to thereby improve or entirely relieve one or more of the symptoms produced by the pimple or acne.

Another aspect of the invention is the hypertonic moisture-containing adhesive patch itself. The patch as noted above contains a flexible backing and a lower hydrophilic, pressure-sensitive adhesive layer containing water, a hydrophilic polymer dispersed in the water, and a dissolved substance. The relative amounts of the solute and solvent are adjusted such that the osmotic pressure of the patch is above that of the underlying tissue of the patient so as to maintain the adhesive hydrogel layer in a hypertonic state. The tacky surface of the adhesive layer wets the skin and creates the hydrophilic bridge with the patient's skin. This allows the free transport of fluid, especially the extracellular fluid contained in the pimple, across the hydrophilic bridge into the patch.

THE FIGURES

FIG. 3 is a top perspective top view of the patch of FIG. 2 showing a portion of the removable liner that covers the adhesive before the patch is used.

FIG. 4 is a greatly enlarged partial cross-sectional view of the patch on line 4—4 of FIG. 3 showing the patch as it appears when applied to the patient's skin over a pimple.

FIG. 4A is a still further enlarged microscopic view showing the lower portion of the patch in contact with the skin over a pimple.

FIG. 5 is a perspective bottom view of the patch of FIG. 3 showing the exposed pressure-sensitive surface after the liner sheet has been removed and before the patch has been applied to the skin.

FIGS. 6A, 6B and 6C show sequential microscopic vertical cross-sectional views of the patch and underlying skin to illustrate the progressive improvement of a pimple as an increasing amount of fluid diffuses from the pimple and surrounding tissue into the hydrogel matrix of the patch.

DETAILED DESCRIPTION OF THE INVENTION

Figure 1:
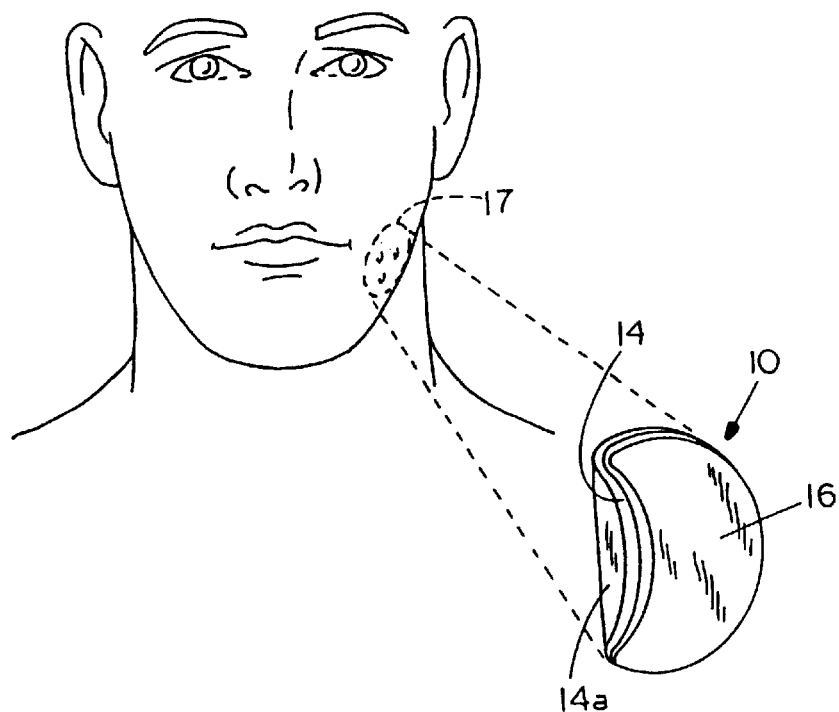
FIG. 1 is a perspective view of a patient with facial acne to which a circular patch according to the present invention is to be applied to cover the acne and the surrounding skin.

In FIG. 1 is shown a patient with facial acne to which a patch 10 in accordance with the invention is to be applied. The patch 10, which in this case is circular, has a water-based hydrogel adhesive layer 14 with a pressure-sensitive surface 14a and a backing layer 16 that provides structural support for the patch and is composed, for example, of cloth, nonwoven fabric, or plastic film. The adhesive layer 14 contains moisture and a dissolved material in sufficient quantity to maintain the osmotic pressure within the patch 10 above that of the tissue, especially the dermis, beneath the upper layer of dead skin (the stratum corneum). During use, the patch 10 is bonded to the skin of the patient by the hydrogel adhesive layer 14 as shown at 17 directly over the acne condition being treated. The hydrogel layer 14 contains enough moisture to hydrate the skin, and the tacky surface 14a of the patch 10 forms hydrophilic bridge with the patient's skin by wetting the normally dry stratum corneum enough to allow the progressive transfer of fluid into the adhesive layer 14 through the stratum corneum which acts as a semi-permeable membrane when hydrated. The patch 10 is left in place for as long as needed, e.g., a day or more, and is replaced whenever necessary. One preferred protocol is to wash the skin and replace the patch twice a day.

Figure 2:
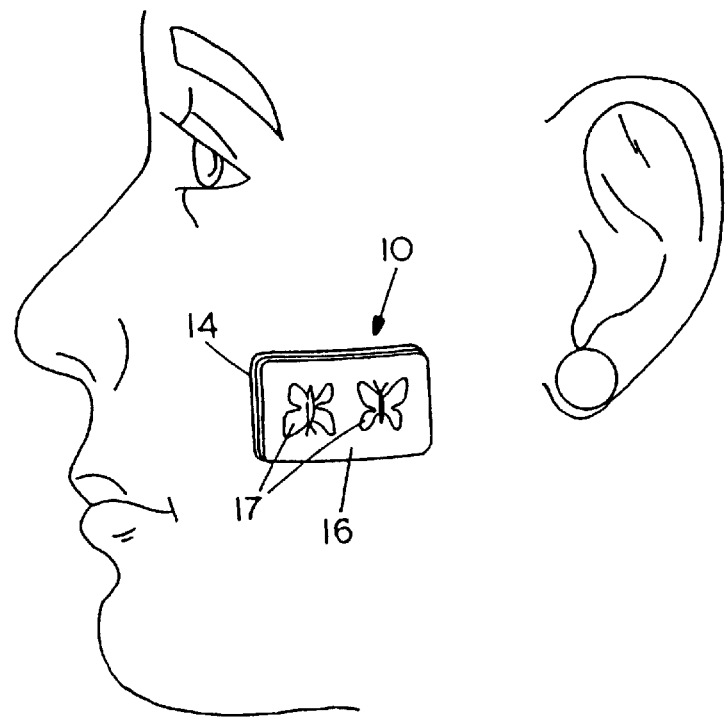
FIG. 2 is a side view of another patient that has a single pimple on the face which is covered by a rectangular hypertonic adhesive patch in accordance with the invention.

FIG. 2 shows another patch 10 which is similar to the patch of FIG. 1 except that it is rectangular in shape. The patch 10 of FIG. 2 is applied to the face of another patient over a single isolated pimple (not shown). This patch has the same structure and composition as that of FIG. 1 except that a rectangular cutting die has been used to produce the rectangular outline shown in FIG. 2. On the outer surface of the backing 16 are printed fanciful designs such as, in this case, a butterfly motif to make the patch 10 more interesting and provide more visual appeal.

Refer now to FIGS. 3–4A which illustrate the structural features of the patch in more detail. The patch 10 in this case is provided with an underlying layer of medical grade, non-irritating, hydrated pressure-sensitive adhesive 14 of any suitable type known to those skilled in the art, for example as described in U.S. Pat. Nos. 5,536,263; 4,675,009; 2,498,338; 3,645,835; 4,427,737 and 4,867,150 (which are incorporated herein by reference) except that the osmotic pressure is controlled as already described by regulating the ratio of solvent (water) to dissolved solutes. The lower surface 14a of adhesive 14 is protected during shipment and storage by a removable liner sheet 18 (FIG. 3) that can comprise any suitable commercially available release paper or plastic film. The liner sheet 18 can be a 2 mil. sheet of polyester film. Before use, the liner sheet 18 is removed to expose the lower surface of the pressure-sensitive adhesive 14. The patch 10 is then applied to the skin 15 and is held in place by the pressure-sensitive adhesive surface 14a, for example, on the face of the patient as shown in FIGS. 1, 2, 4 and 4A. While the pressure-sensitive surface 14a of the hydrogel adhesive layer 14 will hold the patch in contact with the skin 15, the patch 10 can also be held in place more securely if desired by wrapping it with a cloth bandage or by taping down the edges with any suitable commercially available medical adhesive tape (not shown).

The patch 10 for use on the face or upper body is typically about 1 inch long by 1 inch wide and has rounded corners. It can also be circular with a diameter of from about ½ inch to 1½ inches. The backing sheet 16 typically has a thickness of about 3–8 mils and has applied to it about 0.012 ounces per square inch of the adhesive. The backing sheet 16 is typically a flexible sheet of open-cell polyurethane foam, open-cell polyethylene foam, nonwoven fabric or cloth.

The composition of a preferred hydrogel adhesive 14 will now be described in more detail. The hydrogel layer 14 comprises a base or matrix composed of water and a water-dispersible hydrophilic polymer. The hydrophilic polymer contained in the adhesive layer 14 acts as a thickening or gel forming agent that helps the adhesive layer set up once applied to the backing 16. For this purpose, a high molecular weight natural or synthetic polymer and optionally a polymeric tackifier is included as a part of the hydrophilic hydrogel adhesive layer. The hydrophilic polymer can be any natural or synthetic polymer, for example a gum, i.e., a natural plant exudate such as karaya as described in U.S. Pat. No. 5,536,263 which is incorporated herein by reference, starch, kelp, gum or a synthetic hydrophilic polymer such as polyacrylamide, polyacrylic acid or a polyionic gel, e.g., polysodium acrylate, a polyquaternary amine, a polysulfonate, carboxymethylcellulose (CMC), carboxypropylcellulose (CPC), and the like as described in U.S. Pat. No. 5,547,681 which is also incorporated herein by reference. When karaya is used as a thickening or gel forming agent for the hydrogel adhesive layer 14, it has the advantage of providing a bacteriostatic action and thereby reduces bacterial counts.

In order to create the desired osmotic pressure within the patch 10, at least one substance is dissolved in the adhesive hydrogel layer 14. Increasing amounts of this solute will create higher osmotic pressures, since the osmotic pressure of a solution is proportional to the fraction of solute molecules in the solution. Enough solute is used to produce an osmotic pressure greater than that of human tissue, namely over about 308 mOsmol/L. Various solutes can be employed. The most suitable for the present invention comprise soluble carbohydrates including sugar, soluble salts, weak acids and bases, mono- and polyhydric alcohols, soluble amino acids or proteins, and other water soluble molecules. Those proteins that are soluble in water form colloidal solutions. On a weight basis, salts are generally the most effective osmotic enhancers since, at the same temperature, equal volumes of solutions showing the same osmotic pressure contain equal numbers of molecules of the solute. If sucrose which has a molecular weight of 342.3 is used, for example, the osmotic pressure of a molal solution is 24.8 atmospheres at 0° C. Sodium chloride, however, with a molecular weight of 58 is almost six times as effective in increasing the osmotic pressure as the same quantity of sucrose by weight. A few examples of the salts that can be employed are sodium chloride, potassium chloride, calcium chloride, and calcium carbonate. Among the sugars that can be used are sucrose, glucose, levulose, and lactose. Among the weak acids that can be employed are acetic acid, adipic acid, aspartic acid, glutamic acid, and malic acid. Among the weak bases are potassium bicarbonate and sodium bicarbonate. Among the proteins are albumin and casein. Among the amino acids are glycine, alanine, cysteine and leucine. Among the alcohols are ethanol, methanol, glycerin, ethylene glycol, and propylene glycol. Other solutes that can be used will be apparent to those skilled in the art. Naturally, the solute should be non-irritating and unlikely to produce toxic reactions or skin irritation at the concentration used. While amounts will vary depending upon the desired osmotic pressure, salts, if used, are typically present for example at concentrations of about 0.1% to 15% by weight or more, and preferably from about 3.0% to about 5% by weight, to produce an osmotic pressure greater than the fluid within the infected skin. Sugars and proteins are typically used in an amount, for example, from about 1% to 25% by weight.

Solutes can be used in combination. For example, the osmotic pressure increase produced by glycerin can be further increased by the addition of any nontoxic electrolyte, e.g., the addition of 1% sodium chloride. A solution of about 0.9% sodium chloride is isotonic with serum or blood. Accordingly, anything with a higher osmotic pressure than the equivalent of 0.9% sodium chloride is sufficient to be at a greater osmotic pressure than blood or serum. However, in practice it is desirable to have a much higher osmotic pressure in the hydrophilic layer than in the tissue, since the higher the osmotic pressure of the hydrophilic layer, the greater will be the absorption of moisture from the tissue. Moreover, since the permeability of any particular skin area cannot be precisely predicted, it is desirable to keep the osmotic pressure in the adhesive substantially higher than that of the tissue to maintain a high osmotic differential and to provide a margin of error. During use, as water is transported from the tissue into the hydrophilic adhesive layer of the patch, some electrolytes are carried with it, as well as other substances such as small amounts of simple proteins. The water that thus passes through the stratum corneum, which has been hydrated by the patch, dilutes the salt present in the overlying adhesive layer. As the patch 10 is used, dilution of the solute causes the patch to lose effectiveness over time. Consequently, the patch 10 should be removed periodically and replaced with a fresh patch.

The pressure-sensitive hydrocolloidal adhesive layer 14 can be prepared by admixing the constituents just prior to applying the adhesive to the backing 16. Mixing can be accomplished by providing a processing mixer with a cooling jacket through which a coolant such as a chilled mixture of water and ethylene glycol is passed during operation. The components of the hydrogel are continuously added to the mixer during operation. While any suitable mixer can be used, one suitable mixer is a five-inch continuous processing mixer manufactured by Teledyne Readco Company of York, Pa. The coolant passed through the processing mixer can be maintained at about 0° C. The temperature of the moisture-containing hydrogel 14 as it flows onto the exposed surface of the backing sheet 16 is important for controlling the infiltration of the coating into the back sheet 16. The coolant will, under typical operating conditions, keep the extruded hydrogel 14 at a temperature of about 9° C. to 14° C. as it comes into contact with the backing 16. If deeper penetration is desired, the temperature of the hydrogel is lowered to about 9° C. for a typical hydrogel formulation. If less penetration is wanted, the temperature is raised closer to 15° C. The hydrogel adhesive produced by the processing mixer, which is in a chilled fluid condition, is expelled onto backing sheet 16 and is spread out, e.g., by means of a knife coater of suitable known construction.

The backing 16 can be a porous or non-porous self-supporting sheet of water insoluble polymeric material that provides strength and integrity for the adhesive patch 10, and when porous can act as a substrate for receiving and retaining a portion of the adhesive hydrogel 14.

One preferred backing sheet 16 is a lightweight, pliable strip composed, for example, from a nonwoven fabric which consists of polymeric fibers such as polyester, cotton or cellulose fibers bonded together with a sizing resin. The backing sheet 16 should be nonirritating to human skin. If desired, the backing sheet 16 can be coated on its back surface with a release coating such as a silicone release coating as described in U.S. Pat. No. 4,696,854 which is incorporated herein by reference. One suitable release coating is a 100% solids electron beam curable silicone such as TEGO® Resin Acrylates/RC-Series RC 705 and RC 726 by Goldschmidt Chemical Corporation of Hopewell, Va. The preferred backing sheet 16 is a porous polymeric water insoluble nonwoven fibrous fabric. A suitable sizing material for bonding the fibers together is a latex resin.

The backing sheet 16 can comprise other stable, water insoluble flexible sheet materials. Another preferred backing comprises a 5.5 mil. strip of nonwoven fabric formed from a mixture of cellulose fibers derived from wood pulp and polyester fibers. The fibers are assembled loosely into the backing to maintain porosity. A sizing resin is applied to hold the fibers together. The sizing resin can comprise a nonirritating resin applied as a latex emulsion. One example is HYCAR® 26477, a resin produced by B.F. Goodrich Co. of Brecksville, Ohio. Another suitable backing sheet is a nonwoven fabric comprising a wetlay cellulose and polyester nonwoven fabric containing as a sizing an acrylic latex emulsion resin, e.g., product number N7601 by Dexter Corporation of Windsor Locks, Conn.

In another embodiment of the invention, the backing sheet 16 comprises a porous woven 5 mil. acetate polymer cloth sometimes known as "silk cloth." Another form of backing sheet 16 is an open-cell plastic foam strip of low density polyethylene or polyvinyl acetate resin. Other backing sheets that can be used include woven cotton cloth or other cloth formed from a synthetic polymer. Suitable synthetic cloths include nylon, polyester, polyacetate. When the backing sheet 16 is a woven cloth, no sizing resin is needed. When the backing sheet 16 is pervious to air, the patch is non-occlusive to the skin. However, an occlusive backing such as polyethylene film can be used if desired.

After the hydrogel adhesive layer 14 has been applied to the backing 16, the patches can be formed by die-cutting, for example as described in U.S. Pat. No. 5,536,263.

Refer now to FIGS. 4 and 4A which illustrate a cross-sectional view of the patch after application to the skin 15 following removal of the liner sheet 18. As shown in the figures, the patch 10 has been applied over a pimple 20 which is surrounded by a swollen area 22 in the dermis and epidermis. The pimple 20 is covered by the stratum corneum 24 which may have, or may eventually develop, an opening 26 just above the center of the pimple 20. When the opening 26 appears, fluid and necrotic tissue debris will flow out at an increasing rate to be absorbed into the hydrophilic adhesive layer 14 of the patch 10. If should also be noted that the moisture within the adhesive layer 14 soon hydrates the normally dry stratum corneum 24, causing it to swell and to become more flexible. In addition, because of the added moisture, the free transport of fluids from the tissue 15 upwardly into the hydrophilic adhesive gel 14 will be possible over an extended period of time as indicated by the vertical arrows in FIG. 4A. This osmotic effect is beneficial since it enhances drainage of the inflamed nodules. The evaporation of moisture through the porous backing 16 helps to maintain the osmotic differential and thus facilitates continued fluid transport out of the skin.

FIGS. 6A–6C show in timed sequence three microscopic vertical cross-sectional views of the same patch 10 and the underlying skin to illustrate how an increasing amount of interstitial fluid from the tissue and the pimple is progressively carried by osmotic pressure upwardly into the adhesive layer 14. These figures show the progressive improvement of the pimple 20 over time proceeding from FIGS. 6A to 6C as fluid is removed from the skin tissue 15 and from the pimple 20. In FIG. 6A, the pimple 20 is shown without a break in the stratum corneum 24. However, after a few minutes or hours as shown in FIG. 6B, the hypertonic pressure of the adhesive layer 14 will often produce a break or opening 26 through which fluid or pus from within the pimple 20 is withdrawn from the patient's body into the overlying hydrogel adhesive layer 14. The upward flow of fluid from the tissue 15 into the adhesive layer 14 is indicated by vertical arrows in the figures. Finally, as shown in FIG. 6C, the pimple 20 is much reduced as even more fluid is carried by osmotic pressure from the pimple and surrounding tissue into the hydrophilic gel layer 14, thereby expanding the hydrophilic gel layer. When salt is used to create the hypertonic pressure within the adhesive 14, it provides an additional benefit in helping to keep the patch 10 sterile or at least helps to reduce the bacterial count to a safe level.

The invention will be better understood by reference to the examples. The patches are prepared by providing a porous nonwoven flexible fabric backing, e.g., nonwoven fabric having a thickness of 5 mils. To the flexible backing is applied a hydrophilic adhesive composition shown in each example having a thickness of about 3 mils. The hydrophilic adhesive compositions are given in the following examples:

EXAMPLES

Example 1

| Ingredient | % by Weight |
| --- | --- |
| Glycerin | 32.0 |
| Water | 10.0 |
| Propylene Glycol | 20.0 |
| Sodium Chloride | 1.0 |
| Polyquaternary amine | 37.0 |

Example 2

| Ingredient | % by Weight |
| --- | --- |
| Propylene Glycol | 33.0 |
| Water | 20.0 |
| Polyacrylamide | 15.0 |
| Sucrose | 11.0 |
| Maltodextrin | 12.0 |
| Tackifier comprising a vinyl acetate resin emulsion | 9.0 |

Example 3

| Ingredient | % by Weight |
| --- | --- |
| Water | 14.0 |
| Karaya | 10.0 |
| Albumin solids | 45.0 |
| Tackifier comprising an acrylic ester copolymer emulsion adhesive (B.F. Goodrich 26415) | 31.0 |

Example 4

| Ingredient | % by Weight |
| --- | --- |
| Water | 16.0 |
| Ethylene Glycol | 12.0 |
| Acrylic ester copolymer emulsion tackifier | 25.0 |
| Tackifier comprising vinyl acetate/dioctyl maleate copolymer emulsion | 38.0 |
| Polysodium acrylate | 9.0 |

Example 5

| Ingredient | % by Weight |
| --- | --- |
| Glycerol | 58.0 |
| Water | 10.0 |
| Polyacrylamide | 15.0 |
| Polyacrylic acid | 15.0 |
| Calcium chloride | 2.0 |

Example 6

| Ingredient | % by Weight |
| --- | --- |
| Propylene Glycol | 33.0 |
| Water | 20.0 |
| Polysulfonate | 15.0 |
| Sucrose | 11.0 |
| Maltodextrin | 12.0 |
| Tackifier comprising a vinyl acetate resin emulsion | 9.0 |

Example 7

| Ingredient | % by Weight |
| --- | --- |
| Propylene Glycol | 33.0 |
| Water | 20.0 |
| Carboxymethylcellulose (CMC) | 15.0 |
| Sucrose | 11.0 |
| Maltodextrin | 12.0 |
| Tackifier comprising a vinyl acetate resin emulsion | 9.0 |

Example 8

| Ingredient | % by Weight |
| --- | --- |
| Propylene Glycol | 33.0 |
| Water | 20.0 |
| Carboxypropylcellulose (CPC) | 15.0 |
| Sucrose | 11.0 |
| Maltodextrin | 12.0 |
| Tackifier comprising a vinyl acetate resin emulsion | 9.0 |

Example 9

| Ingredient | % by Weight |
| --- | --- |
| Glycerin | 49 |
| Nonionic and/or ionic polyacrylamide | 16 |
| Acrylic ester copolymer adhesive | 8 |
| Malto dextrin | 6 |
| Pectin | 4 |
| Deionized water | 6.6 |
| Proplylene glycol | 6.45 |
| Salicylic acid | 2 |
| Sodium chloride | 1.95 |

Example 10

| Ingredient | % by Weight |
| --- | --- |
| Glycerin | 49 |
| Nonionic and/or ionic polyacrylamide | 16 |
| Acrylic ester copolymer adhesive | 8 |
| Malto dextrin | 6.25 |
| Pectin | 4 |
| Deionized water | 7 |
| Proplylene glycol | 7 |
| Salicylic acid | 2 |
| Sodium chloride | 0.75 |

The adhesives described above are applied to the backing 16 to provide a thin adhesive layer which is covered by a removable slip sheet or liner sheet 18 of any suitable commercially available composition. The patches 10 are then packaged in protective paper or plastic wrappers, pouches or envelopes for distribution. Also contained in the package, e.g., by being printer on the pouch or envelope, are directions for treating acne or pimples by removing the liner sheet 18 and applying the patch to the skin directly over the pimple or acne. The user or health care worker can easily remove the patches from the envelope, remove the protective liner sheet, and apply the patch directly to the acne or pimple. The contact between the gel and the skin consequently results in an osmotic gradient, pulling the fluid from the pimples and imflamed skin through the hydrated stratum corneum into the patch, thereby reducing fluid within the skin. It is therefore also useful in treating eczema.

The patch 10 in accordance with the invention can be either non-sterile or, if desired, sterilized as described for example in U.S. Pat. No. 4,307,717 which is incorporated herein by reference.

If desired, any of the hydrophilic hydrogel adhesive compositions in accordance with the present invention can have dispersed therein one or more antimicrobial agents including but not limited to any of the following: isopropyl alcohol, povidone iodine, mercurochrome, hydrogen peroxide, benzoyl peroxide, retinoic acid, miconazole, acyclovir, tetracycline, chlorohexidine gluconate, erythromycin, isotretinoin, hexachlorophene, silver nitrate, acetic acid, salicyclic acid and the like.

Many variations of the present invention within the scope of the appended claims will be apparent to those skilled in the art once the principles described herein are understood.

What is claimed is:

1. A method of treating acne or an isolated pimple on a patient comprising applying to the acne or isolated pimple of the patient in need of such treatment an adhesive patch comprising a flexible water insoluble backing having a front side and a back side and a hydrogel positioned on at least a portion of the front side of the flexible backing; wherein the hydrogel comprises:

water;

glycerin;

a thickening agent or gel forming agent dispersed in the water or glycerin;

an adhesive;

a water soluble solute dissolved in the water or glycerin in sufficient quantity to raise the osmotic pressure of the hydrogel above 308 mOsmol/L.

2. The method of claim 1 wherein the hydrogel hydrates at least an upper layer of the skin surface of the patient to form a hydrophilic bridge with the skin surface of the patient and the hydrogel.

3. The method of claim 2 wherein the hydrophilic bridge allows fluid transport between the skin surface of the patient and the adhesive patch across the hydrophilic bridge so that interstitial fluid in and around the acne or isolated pimple is then transported through the stratum corneum by osmotic pressure into the hydrogel to thereby improve or entirely relieve one or more of the symptoms produced by the pimple or acne.

4. The method of claim 1 wherein the patch is applied to the skin surface of the patient to cover the entire surface of the acne or isolated pimple.

5. The method of claim 1 wherein the patch effectively reduces extracellular fluid associated with acne or an isolated pimple, swelling associated with acne or a pimple, inflammation associated with acne or a pimple, or a combination thereof.

6. The method of claim 1 wherein the patient is a human.

7. The method of claim 1 wherein the patch is applied to the face of the patient.

8. A method of treating acne or an isolated pimple on a patient comprising applying to the acne or isolated pimple of the patient in need of such treatment an adhesive patch comprising a flexible water insoluble backing having a front side and a back side and a hydrogel positioned on at least a portion of the front side of the flexible backing; wherein the hydrogel comprises:

a liquid;

a thickening agent or gel forming agent dispersed in the liquid;

an adhesive;

a solute dissolved in the liquid in sufficient quantity to raise the osmotic pressure of the hydrogel above 308 mOsmol/L.

9. The method of claim 8 wherein the liquid comprises water.

10. The method of claim 8 wherein the liquid comprises glycerin.

11. The method of claim 8 wherein the flexible water insoluble backing comprises woven fabric, nonwoven fabric, or a combination thereof.

12. The method of claim 8 wherein the flexible water insoluble backing comprises polyester, nylon, polyacetate, cotton, cellulose fibers, paper, cloth, plastic, open-cell polyurethane foam, open-cell polyethylene foam, or a combination thereof.

13. The method of claim 8 wherein the thickening agent or gel forming agent is a water-dispersible hydrophilic polymer.

14. The method of claim 9 wherein the water-dispersible hydrophilic polymer is a natural polymer.

15. The method of claim 9 wherein the water-dispersible hydrophilic polymer is a synthetic polymer.

16. The method of claim 9 wherein the water-dispersible hydrophilic polymer is a gum, a natural plant exudate, karaya, starch, cornstarch, kelp, polyacrylamide, polyacrylic acid, a polyionic gel, polysodium acrylate, a polyquaternary amine, a polysulfonate, carboxymethylcellulose, carboxypropylcellulose, maltodextrin, pectin, or a combination thereof.

17. The method of claim 8 wherein the adhesive comprises a vinyl acetate resin emulsion, an acrylic ester copolymer emulsion, a vinyl acetate/dioctyl maleate copolymer emulsion, an acrylic ester copolymer adhesive, or a combination thereof.

18. The method of claim 8 wherein the liquid soluble solute is a carbohydrate, a salt, a weak acid, a weak base, a monohydric alcohol, a polyhydric alcohol, an amino acid, a protein, or a combination thereof.

19. The method of claim 18 wherein the carbohydrate is sucrose, glucose, levulose, lactose, or a combination thereof.

20. The method of claim 18 wherein the carbohydrate is present in about 1 wt. % to about 25 wt. % of the hydrogel.

21. The method of claim 18 wherein the salt is sodium chloride, potassium chloride, calcium chloride, calcium chloride, calcium carbonate, or a combination thereof.

22. The method of claim 18 wherein the salt is present in about 0.1 wt. % to about 15 wt. % of the hydrogel.

23. The method of claim 18 wherein the salt is present in about 3 wt. % to about 5 wt. % of the hydrogel.

24. The method of claim 18 wherein the weak acid is acetic acid, adipic acid, aspartic acid, glutamic acid, malic acid, or a combination thereof.

25. The method of claim 18 wherein the weak base is potassium bicarbonate, sodium bicarbonate, or a combination thereof.

26. The method of claim 18 wherein the protein is albumin, casein, or a combination thereof.

27. The method of claim 18 wherein the protein is present in about 1 wt. % to about 25 wt. % of the hydrogel.

28. The method of claim 18 wherein the amino acid is glycine, alanine, cysteine, leucine, or a combination thereof.

29. The method of claim 18 wherein the monohydric alcohol is methanol, ethanol, or a combination thereof.

30. The method of claim 18 wherein the polyhydric alcohol is glycerin, ethylene glycol, propylene glycol, or a combination thereof.

31. The method of claim 8 wherein the hydrogel further comprises one or more antimicrobial agents.

32. The method of claim 31 wherein the antimicrobial agent is isopropyl alcohol, povidone iodine, mercurochrome, hydrogen peroxide, benzoyl peroxide, retinoic acid, miconazole, acyclovir, tetracycline, chlorohexidine gluconate, erythromycin, isotretinoin, hexachlorophene, silver nitrate, acetic acid, salicylic acid, or a combination thereof.

33. The method of claim 8 wherein the adhesive patch further comprises a removable liner releasably mounted on the front side of the flexible backing.

34. The method of claim 33 wherein the release liner is manufactured from a polyester film.

35. The method of claim 8 wherein the adhesive patch is circular.

36. The method of claim 8 wherein the adhesive patch has a diameter of about 0.5 inch to about 1.5 inches.

37. The method of claim 8 wherein the adhesive patch is rectangular.

38. The method of claim 8 wherein the flexible water insoluble backing has a thickness of about 3 mm to about 8 mm.

* * * * *